United States Patent
Imagawa et al.

(10) Patent No.: US 9,986,962 B2
(45) Date of Patent: Jun. 5, 2018

(54) MEDICAL IMAGE DISPLAY APPARATUS AND X-RAY DIAGNOSIS APPARATUS

(71) Applicant: Toshiba Medical Systems Corporation, Otawara-shi (JP)

(72) Inventors: Kazuo Imagawa, Nasushiobara (JP); Takuya Sakaguchi, Utsunomiya (JP); Ryuji Zaiki, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 6 days.

(21) Appl. No.: 14/692,384

(22) Filed: Apr. 21, 2015

(65) Prior Publication Data

US 2015/0223769 A1    Aug. 13, 2015

Related U.S. Application Data

(63) Continuation of application No. PCT/JP2013/083306, filed on Dec. 12, 2013.

(30) Foreign Application Priority Data

Dec. 12, 2012   (JP) ................................. 2012-271196
Dec. 11, 2013   (JP) ................................. 2013-256504

(51) Int. Cl.
*A61B 6/02*       (2006.01)
*A61B 6/00*       (2006.01)
(Continued)

(52) U.S. Cl.
CPC .............. *A61B 6/466* (2013.01); *A61B 6/022* (2013.01); *A61B 6/4441* (2013.01); *A61B 6/463* (2013.01);
(Continued)

(58) Field of Classification Search
CPC ......... A61B 6/022; A61B 6/463; A61B 6/466; A61B 6/467; A61B 6/4441; A61B 6/54;
(Continued)

(56) References Cited

U.S. PATENT DOCUMENTS 2,712,608 A * 7/1955 Atwell ................... A61B 6/022
                                                      33/1 C
6,031,565 A * 2/2000 Getty ..................... A61B 6/022
                                                      348/51
(Continued)

FOREIGN PATENT DOCUMENTS

JP      2001-070293 A      3/2001
JP      2005-349127 A     12/2005
(Continued)

OTHER PUBLICATIONS

International Search Report dated Feb. 10, 2014 for PCT/JP2013/083306 filed on Dec. 12, 2013 with English Translation.
(Continued)

*Primary Examiner* — Irakli Kiknadze
(74) *Attorney, Agent, or Firm* — Oblon, McClelland, Maier & Neustadt, L.L.P.

(57) ABSTRACT

According to an embodiment, a medical image display apparatus is accessible to an external device that stores data of a plurality of X-ray images with different imaging angles, or includes a storage unit that stores the data of the plurality of X-ray images. The medical image display apparatus includes a display, a distance specifying unit, an image selector and a display controller. The distance specifying unit specifies a distance of a user to the display. The image selector selects, from the plurality of X-ray images, two X-ray images with an angular difference determined based
(Continued)

on the distance of the user. The display controller displays the selected two X-ray images on the display for stereopsis by the user.

12 Claims, 8 Drawing Sheets

(51) Int. Cl.
*G10L 25/48* (2013.01)
*H04N 13/04* (2006.01)
*G10L 15/00* (2013.01)
*G10L 15/22* (2006.01)

(52) U.S. Cl.
CPC .............. *A61B 6/467* (2013.01); *A61B 6/54* (2013.01); *A61B 6/548* (2013.01); *G10L 25/48* (2013.01); *H04N 13/0402* (2013.01); *G10L 15/00* (2013.01); *G10L 2015/223* (2013.01)

(58) Field of Classification Search
CPC ... A61B 6/548; G10L 15/00; G10L 2015/223; G10L 25/48; H04N 13/0402; G06F 19/322; G06F 17/3089; G06F 19/327; G06F 21/6254; G06F 19/328; G06F 21/6263; G06F 19/325; G06F 19/3406; G06F 19/3443; G06F 21/6245; G06F 17/30867; G06F 17/30923; G06F 19/321; G06F 19/326; G06F 19/3418; G06F 19/34

USPC ............. 378/41, 62; 382/132; 345/8, 6, 419
See application file for complete search history.

(56) References Cited

U.S. PATENT DOCUMENTS

| | | | |
|---|---|---|---|
| 7,567,648 B2 | 7/2009 | Tsubaki et al. | |
| 2010/0231504 A1* | 9/2010 | Bloem | G06F 3/013 345/156 |
| 2012/0200495 A1* | 8/2012 | Johansson | G06F 3/011 345/156 |
| 2013/0002657 A1* | 1/2013 | Sugiyama | A61B 6/02 345/419 |

FOREIGN PATENT DOCUMENTS

| | | |
|---|---|---|
| JP | 2012-61188 | 3/2012 |
| JP | 2012-165358 A | 8/2012 |
| JP | 2012-221290 A | 11/2012 |

OTHER PUBLICATIONS

Written Opinion dated Feb. 10, 2014 for PCT/JP2013/083306 filed on Dec. 12, 2013.
Japanese Office Action dated Feb. 6, 2018 in Japanese Application No. 2013-256504, 4 pages.

* cited by examiner

| No. | Gesture movement shape | Word | Sound | Command |
|---|---|---|---|---|
| 1 | → | "Narrow" | Sound of two-time handclapping | Make parallax narrower |
| 2 | ← | "Widen" | Sound of one-time handclapping | Make parallax wider |
| ⋮ | ⋮ | ⋮ | | ⋮ |
| Z | ⌐↵ | "Adjust" | Sound of three-time handclapping | Execute face recognition process |

MEDICAL IMAGE DISPLAY APPARATUS AND X-RAY DIAGNOSIS APPARATUS

CROSS-REFERENCE TO RELATED APPLICATION

This application is a Continuation Application of PCT Application No. PCT/JP2013/083306, filed Dec. 12, 2013 and based upon and claiming the benefit of priority from prior Japanese Patent Applications No. 2012-271196, filed Dec. 12, 2012 and No. 2013-256504, filed Dec. 11, 2013, the entire contents of all of which are incorporated herein by reference.

FIELD

Embodiments described herein relate generally to a medical image display apparatus and an X-ray diagnosis apparatus, which include a technique of image stereopsis.

BACKGROUND

There is known a technique of image stereopsis, which enables stereoscopic visual perception of an image by displaying on a monitor a left-eye image and a right-eye image which have an angular difference. The image stereopsis can make it possible for a user to easily recognize a front-and-rear relation of objects and information of irregularities on surfaces of objects, which are difficult to recognize with ordinary two-dimensional displays. In recent years, the technique of image stereopsis has begun to be applied to the medical field. With the technique of image stereopsis being applied to medical treatment, for example, even in a state in which the position of a diseased part and the position of a blood vessel overlap, a user can grasp the positional relationship thereof. By stereoscopically viewing a target part, the user can perform, for example, a safe, high-precision operation. In order to enable the user to view stereoscopic video relating to a target part, it is necessary that a left-eye image and a right-eye image, which have an optimal angular difference, be displayed on the monitor.

However, the optimal angular difference of each individual user varies depending on the inter-pupil distance of the user, the distance between the user and the monitor, and the sensitivity of the user. For example, in operations and medical treatments, since a plurality of persons are involved, there is a case in which the user who views the monitor changes from time to time. In addition, there is a case in which the distance from the user to the monitor varies due to the movement of the monitor and the movement of the user. Thus, there is such a problem that the stereoscopic video, which is displayed on the monitor, can be viewed by only a limited person or within a limited range.

DETAILED DESCRIPTION

In general, according to an embodiment, a medical image display apparatus is accessible to an external device that stores data of a plurality of X-ray images with different imaging angles, or includes a storage unit that stores the data of the plurality of X-ray images. The medical image display apparatus includes a display, a distance specifying unit, an image selector and a display controller. The distance specifying unit specifies a distance of a user to the display. The image selector selects, from the plurality of X-ray images, two X-ray images with an angular difference determined based on the distance of the user. The display controller displays the selected two X-ray images on the display for stereopsis by the user.

A medical image display apparatus 2 according to the embodiment is described with reference to the accompanying drawings. Incidentally, in the description below, the structural elements having substantially the same functions and structures are denoted by like reference numerals, and an overlapping description will be given only where necessary.

The medical image display apparatus 2 according to the embodiment is applicable either as a single body, or in a mode in which the medical image display apparatus 2 is assembled in an X-ray diagnosis apparatus. In the embodiment to be described below, for the purpose of simple description, an apparatus, in which the medical image display apparatus 2 is assembled in an X-ray diagnosis apparatus including a C-shaped arm, is described by way of example. Incidentally, the medical image display apparatus 2 may be in another modality, for example, may be assembled in a CT apparatus.

Figure 1:
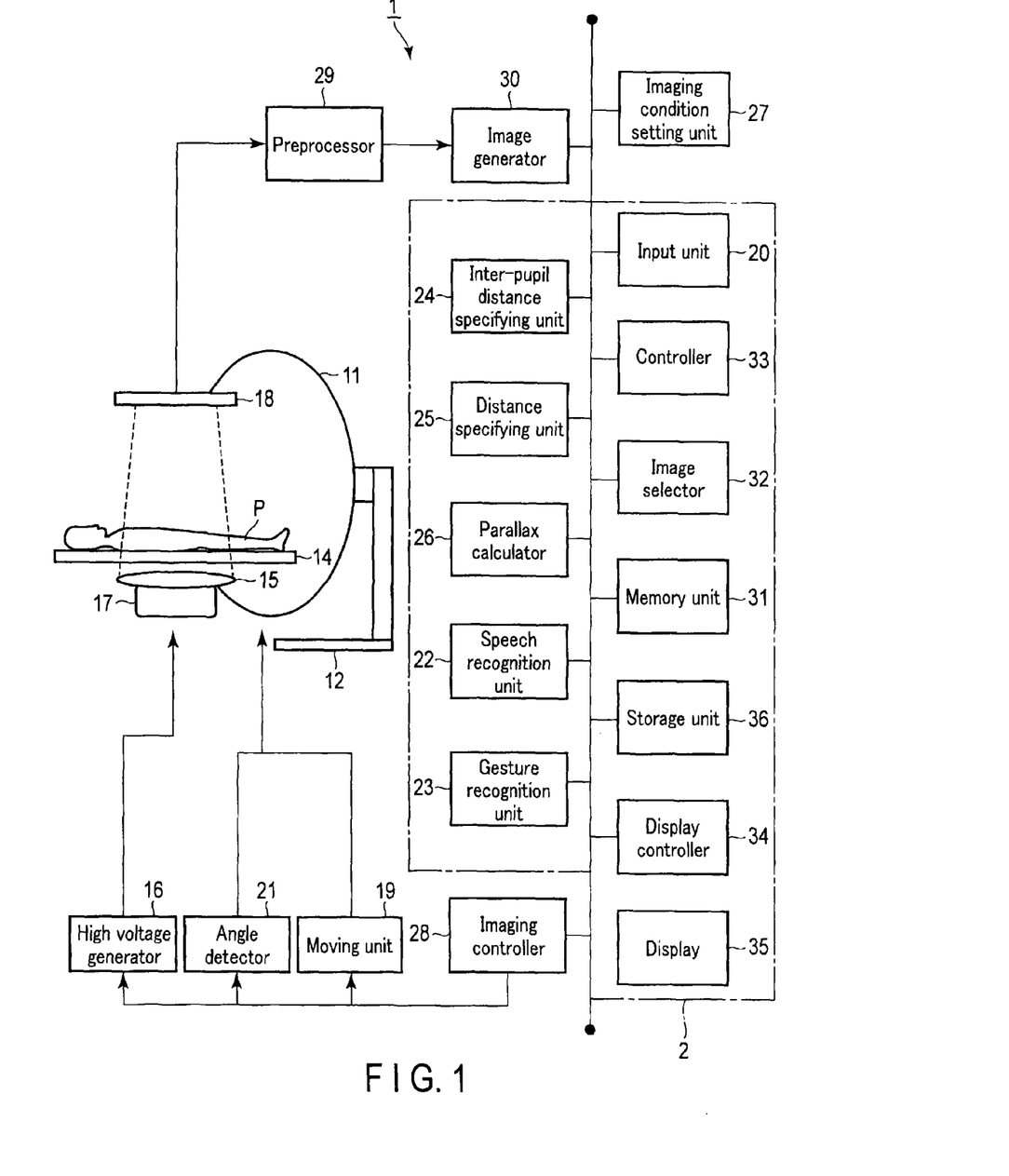
FIG. 1 is a block diagram illustrating an example of a configuration of an X-ray diagnosis apparatus according to an embodiment.

FIG. 1 is a block diagram illustrating an example of a configuration of an X-ray diagnosis apparatus 1 according to the embodiment. As illustrated in FIG. 1, the X-ray diagnosis apparatus 1 includes an X-ray imaging section relating to X-ray imaging, and the medical image display apparatus 2 relating to image processing and image display. The X-ray imaging section includes a C-shaped arm 11, a C-shaped arm support mechanism 12, a bed 13, a tabletop 14, an X-ray generator 15, a high voltage generator 16, an X-ray stop 17, an X-ray detector 18, a moving unit 19, an angle detector 21, an imaging condition setting unit 27, an imaging controller 28, a preprocessor 29, and an image generator 30. On the other hand, the medical image display apparatus 2 includes an input unit 20, a speech recognition unit 22, a gesture recognition unit 23, an inter-pupil distance specifying unit 24, a distance specifying unit 25, a parallax calculator 26, a memory unit 31, an image selector 32, a controller 33, a display controller 34, a display 35, and a storage unit 36.

A frame section of the X-ray imaging section includes the C-shaped arm 11, C-shaped arm support mechanism 12, bed 13 and tabletop 14. The C-shaped arm support mechanism 12 rotatably supports the C-shaped arm 11. The C-shaped arm 11 holds the X-ray generator 15 at one end thereof. The X-ray generator 15 is a vacuum tube which generates X-rays. The X-ray generator 15 generates X-rays by the application of a high voltage (tube voltage) from the high voltage generator 16. The X-ray generator 15 includes an irradiation window for radiating the generated X-rays. The X-ray stop 17 is attached to the irradiation window of the X-ray generator 15. The X-ray stop 17 is a beam limiter which can adjust an X-ray irradiation field on a detection surface of the X-ray detector 18. With the X-ray irradiation field being adjusted by the X-ray stop 17, unnecessary exposure on a subject can be reduced. The C-shaped arm 11 holds the X-ray detector 18 at the other end thereof, such that the X-ray detector 18 is opposed to the X-ray generator 15. The X-ray detector 18 includes a plurality of X-ray detection elements. The plural X-ray detection elements are arranged in a two-dimensional array. The detector having the two-dimensional array shape is called FPD (Flat Panel Detector). Each element of the FPD detects X-rays which have been radiated from the X-ray generator 15 and have passed through the subject. Each element of the FPD outputs an electric signal corresponding to the intensity of the detected X-rays. A line connecting the focus of the irradiation window of the X-ray generator 15 and the center position of the X-ray detection surface of the X-ray detector 18 is called "imaging axis (fifth rotational axis)". The rotation of the X-ray detector 18 about the fifth rotational axis determines the upper/lower side of a photographed image.

Figure 2:
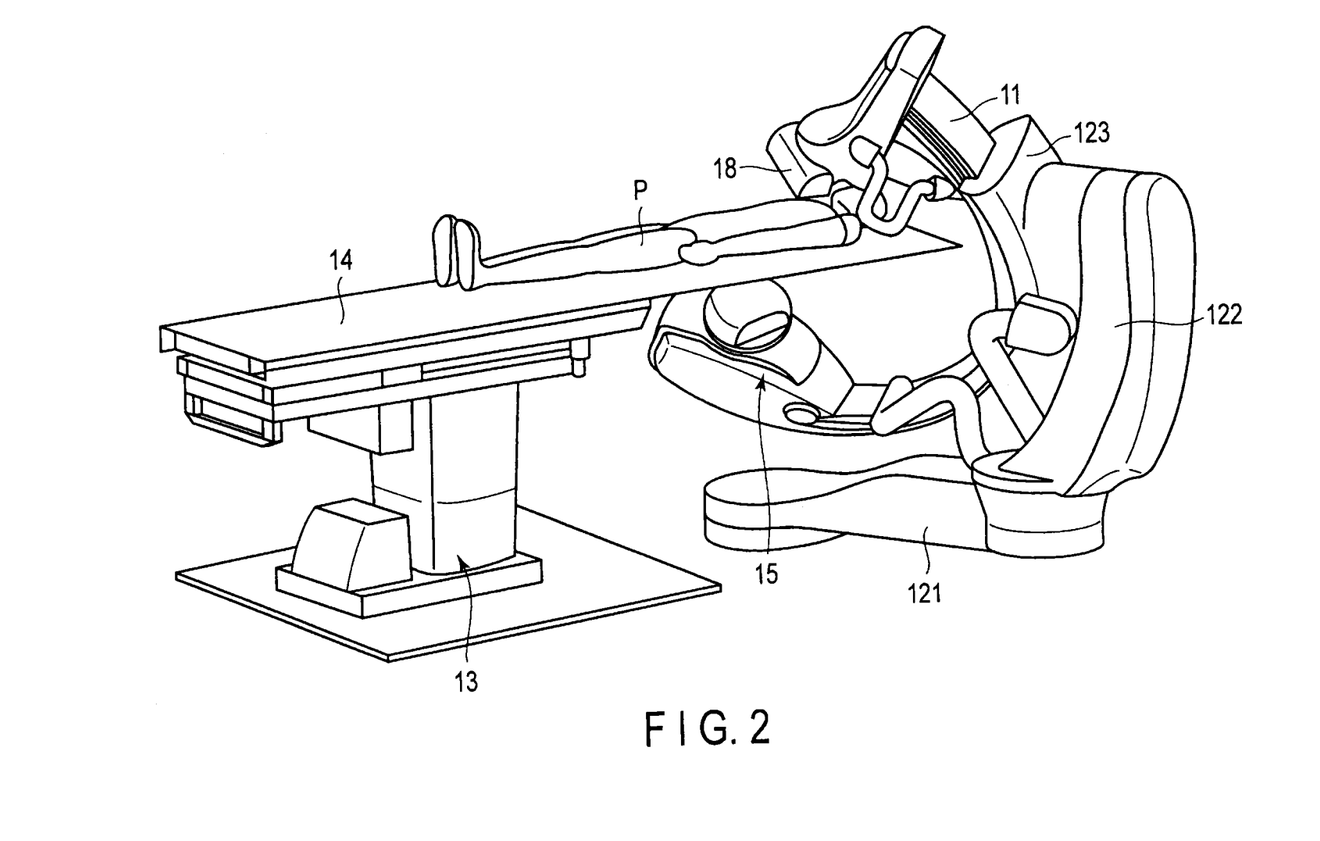
FIG. 2 is a view illustrating an external appearance of a frame section of the X-ray diagnosis apparatus according to the embodiment.

FIG. 2 is a view illustrating an external appearance of the frame section of the X-ray diagnosis apparatus 1 according to the embodiment. Incidentally, the C-shaped arm support mechanism 12 may be either of a ceiling suspension type in which the C-shaped arm 11 is suspended from the ceiling and held, or of a floor type in which the C-shaped arm 11 is held by a mechanism disposed on the floor. In the present embodiment, the floor type is described by way of example. The C-shaped arm support mechanism 12 includes a floor rotary arm 121, a stand 122 and an arm holder 123. The floor rotary arm 121 is provided, at one end thereof, on the floor such that the floor rotary arm 121 is rotatable about a first rotational axis. The stand 122 is supported at the other end of the floor rotary arm 121 such that the stand 122 is rotatable about a second rotational axis. The first and second rotational axes are substantially parallel to an orthogonal axis. The arm holder 123 is supported on the stand 122 such that the arm holder 123 is rotatable about a third rotational axis. The third rotational axis is an axis which is substantially perpendicular to the orthogonal axis. The C-shaped arm 11 is supported on the arm holder 123 such that the C-shaped arm 11 is rotatable (slide rotation) in an arcuate shape along the shape of the C-shaped arm 11. The rotational axis of this slide rotation is referred to as a fourth rotational axis. In the meantime, the C-shaped arm support mechanism 12 may support the C-shaped arm 11 such that the C-shaped arm 11 is movable in a major-axis direction and a minor-axis direction, which will be described later.

The bed 13 and tabletop 14 are disposed between the X-ray generator 15 and X-ray detector. The bed 13 supports the tabletop 14 on which the subject is placed, such that the tabletop 14 is movable in three orthogonal axes. It is assumed that the three orthogonal axes are defined by, for example, a minor axis of the tabletop 14, a major axis of the tabletop 14, and an orthogonal axis which is perpendicular to the minor axis and major axis. Hereinafter, a direction along the major axis of the tabletop 14 is referred to as a major-axis direction. In addition, a direction along the minor axis is referred to as a minor-axis direction. Besides, a direction along the orthogonal axis is referred to as an orthogonal-axis direction.

The moving unit 19 rotates the C-shaped arm support mechanism 12 independently about the first to fifth rotational axes in accordance with control by the imaging controller 28 (to be described later). In addition, the moving unit 19 slidingly moves the tabletop 14 in the major-axis direction or minor-axis direction and elevates the tabletop 14 in the orthogonal-axis direction, in accordance with control by the imaging controller 28 (to be described later). Furthermore, in order to incline the tabletop 14 relative to the surface of disposition of the bed 13, the moving unit 19 rotates the tabletop 14 about a rotational axis which is an axis parallel to at least one of the major-axis direction and minor-axis direction. Hereinafter, as regards the movement of the C-shaped arm 11, slide movement, elevation movement and rotational movement are comprehensively referred to as "movement".

The input unit 20 functions as an interface for accepting instruction information by the user for the X-ray diagnosis apparatus 1. In the present embodiment, "user" means a doctor or the like, who performs a therapy technique, medical treatment, etc. on the subject. The instruction information is, for instance, an X-ray imaging condition and an angle condition of X-ray imaging. The X-ray imaging condition is, for instance, a tube current, a tube voltage, and an imaging time. The angle condition of X-ray imaging is a condition relating to an imaging operation, such as an interval of imaging angles, the number of times of imaging, and a fixed parallax. The fixed parallax is a fixed value of parallax corresponding to a user distance which is prestored in the memory unit 31 (to be described later). The fixed parallax is determined, for example, by a viewing distance of the user to the display 35 (to be described later) and a standard human inter-pupil distance. The fixed parallax can properly be varied in accordance with a user instruction.

In addition, the angle condition may be the fixed parallax, a user's viewing estimated longest distance (hereafter, simply referred to as "longest distance") to the display 35 (to be described later), and the number of times of imaging. The fixed parallax is a parallax at a user's viewing standard distance to the display 35 (to be described later). Thus, a parallax at the longest distance is calculated by the parallax calculator 26 (to be described later), based on the fixed parallax and the longest distance. Similarly, a parallax at a shortest distance is calculated. Then, the range of parallax corresponding to the range of the estimated user's viewing distance is understood, and the interval of the imaging angles can be derived based on the range of parallax and the number of times of imaging.

As the input unit 20, use can properly be made of an input device such as a mouse, a keyboard, a trackball, a touch panel, a button, etc. Specifically, the input unit 20 includes an operation board for moving the C-shaped arm 11 in accordance with a user instruction. The operation board includes a button, a handle, a trackball, etc. for rotating the C-shaped arm 11 independently about the above-described plural rotational axes.

In addition, the input unit 20 accepts an input of a line of sight and an imaging rotational direction.

The line of sight is a direction of an imaging part of the subject, stereoscopic video of which is to be displayed on the display 35 (to be described later). The imaging rotational direction is a rotational direction of the C-shaped arm 11. The X-ray diagnosis apparatus 1 performs an imaging operation along the imaging rotational direction. Positions along this imaging rotational direction include a position corresponding to the line of sight.

The line of sight and the imaging rotational direction are determined by a user operation on an input screen. As the input screen, an image for alignment for inputting the line of sight and the imaging rotational direction is displayed on the display 35. The image for alignment is, for instance, an X-ray image captured as an image for alignment by the X-ray diagnosis apparatus 1, or a model image for alignment. The user can input the line of sight by determining, on the image for alignment, the center position of the subject which is displayed on the display 35. In addition, the user can determine the imaging rotational direction by determining the upper and lower sides of the image of the subject, which is displayed on the display 35.

Incidentally, the image for alignment may be an image photographed by an X-ray CT apparatus which is disposed near the present X-ray diagnosis apparatus 1. At this time, since the X-ray diagnosis apparatus 1 and the X-ray CT apparatus are systems which share the tabletop 14, the tabletop coordinate system of the image for alignment by the X-ray CT apparatus and the the tabletop coordinate system of the X-ray diagnosis apparatus 1 are aligned. Thereby, the positional relationship of the subject between the X-ray diagnosis apparatus 1 and the X-ray CT apparatus is associated.

In addition, the method of inputting the line of sight and the imaging rotational direction may be a method in which the user operates the operation board to move the C-shaped arm to the light of sight, and the button relating to the determination of the line of sight is pressed by the user, thereby determining the line of sight. At this time, the imaging rotational direction is determined by the direction of the detection surface of the X-ray detector 18 which is rotated about the fifth rotational axis. Specifically, in the case where the up-and-down direction of the X-ray detection surface in the X-ray detector corresponds to the up-and-down direction of the X-ray image which is generated by the image generator 30, the imaging rotational direction of the C-shaped arm 11 is set to be the left-and-right direction of the X-ray detection surface which is set by the user. In addition, the imaging rotational direction may be set to be a direction about the fourth rotational axis or the third rotational axis at the timing at which the button relating to the determination of the line of sight was pressed by the user.

Figure 3:
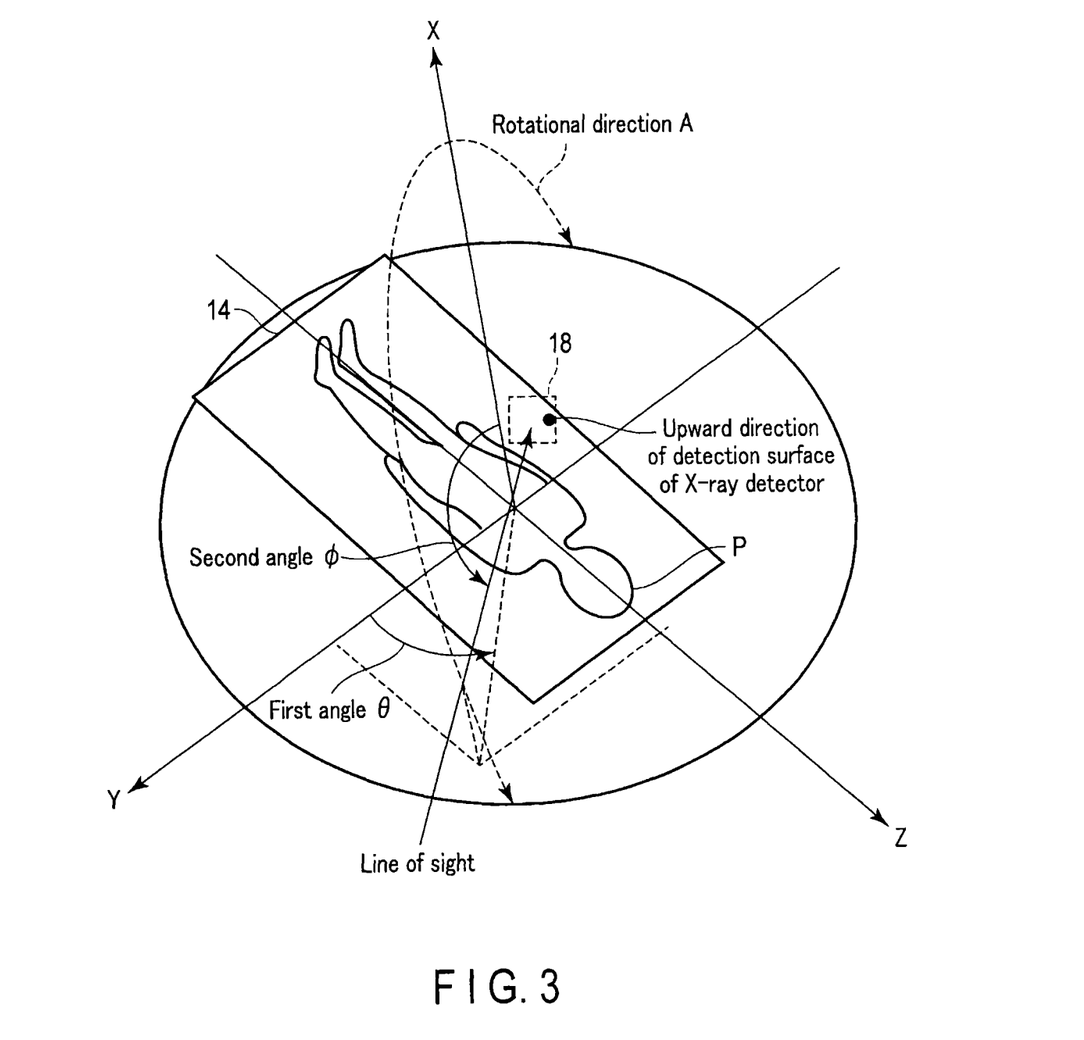
FIG. 3 is an explanatory view for explaining a line of sight, a line-of-sight angle, and an imaging rotational angle of a C-shaped arm.

FIG. 3 is an explanatory view for explaining the line of sight, the line-of-sight angle, and the imaging rotational angle of the C-shaped arm 11. FIG. 3 is an example of an input screen for inputting the line of sight and the imaging rotational angle. The state in which a patient P is placed on the tabletop 14 is displayed. In FIG. 3, the axis along the orthogonal axis is set to be the X axis, the axis along the minor axis is set to be the Y axis, and the axis along the major axis is set to be the Z axis. The user inputs the line of sight on the input screen in FIG. 3. The angle corresponding to the line of sight (hereinafter referred to as "line-of-sight angle") is represented by a first angle $\theta$ formed relative to the Y axis, and a second angle $\varphi$ formed relative to the X axis. In order to set the line of sight, the user may input the first angle $\theta$ and second angle $\varphi$. As illustrated in FIG. 3, in the case where the upward direction of the detection surface of the X-ray detector 18 is set by the user, the imaging rotational direction of the C-shaped arm 11 is set to be a rotational direction A which is the left-and-right direction of the detection surface. In addition, the rotational direction A may be set to be a direction along the slide rotation direction.

The angle detector 21 detects five rotational angles corresponding to the first to fifth rotational axes. Then, the data of the angles detected by the angle detector 21 is added to image data which is output from the X-ray detector 18. At this time, the angles may preferably be in a tabletop coordinate system, but it may be in a coordinate system such as a subject coordinate system or an examination room coordinate system.

The speech recognition unit 22 includes an audio input device, such as a microphone, for detecting speech of the user. The speech of the user is, for instance, voice uttered by the user and sound produced by the user. The microphone is disposed at such a position that the user's speech can be input. For example, the microphone may be attached to the display 35 (to be described later). The speech recognition unit 22 correlates a speech waveform, which was input through the microphone, with a plurality of speech waveforms which are registered in a command DB (Data Base) stored in the memory unit 31 (to be described later). If the input speech waveform substantially agrees with a specific speech waveform registered in the command DB, the speech recognition unit 22 recognizes this input speech waveform. Then, based on the command DB, the speech recognition unit 22 transmits a command, which corresponds to the recognized speech waveform, to the respective components. Incidentally, by the above-described speech recognition technique, the speech recognition unit 22 can distinguish whether the detected speech is speech uttered by an intended user. In the meantime, it is not necessary that the intended user is limited to one person who performs a therapy technique and medical treatment on the subject, and there may be a plurality of users who are targets of speech recognition. In this case, voices of target users of speech recognition may be preregistered in the X-ray diagnosis apparatus 1.

The gesture recognition unit 23 is a detection device including a camera, etc., for detecting a gesture movement of the user. The camera is attached, for example, at an upper part or a lower part of the display 35 (to be described later), and photographs the user. The gesture recognition unit 23 detects and tracks, for example, the user's hand as a specific part, from a plurality of images relating the photographed user, and detects the shape of the gesture movement. The gesture recognition unit 23 correlates the shape of the detected gesture movement with a plurality of gesture movement shapes registered in the command DB stored in the memory unit 31 (to be described later). Then, if the shape of the gesture movement, which substantially agrees with the shape of the detected gesture movement, is registered in the command DB, the gesture recognition unit 23 recognizes this gesture movement. The gesture recognition unit 23 sends a command, which corresponds to the shape of the recognized gesture movement, to the respective components. Incidentally, based on the photographed image, the gesture recognition unit 23 can detect the face of the person who executed the gesture movement, and can specify whether the detected person is the intended user. In addition, the user, who is the target of the gesture movement may have, for example, a tag or the like on the cap, clothes, etc., for distinction from other persons, and the gesture cognition unit 23 may detect this tag, thereby determining whether or not the user is the detection target of the gesture movement.

The inter-pupil distance specifying unit 24 includes a detection device for specifying the inter-pupil distance of the user. The detection device is, for instance, a camera, etc. The camera is attached, for example, at an upper part or a lower part of the display 35 (to be described later), and photographs the user in every specific cycle. The specific cycle is preset, and can properly be varied by the user. Incidentally, the inter-pupil distance specifying unit 24 and the above-mentioned distance specifying unit 25 may be a common detection device. From each image relating to the face of the photographed user, the inter-pupil distance specifying unit 24 extracts a range corresponding to both eyes, for example, based on luminance values. Then, the inter-pupil distance specifying unit 24 specifies the inter-pupil distance on the image from the extracted range corresponding to both eyes. In addition, the inter-pupil distance specifying unit 24 sends the data of the specified inter-pupil distance to the parallax calculator 26.

The distance specifying unit 25 specifies the distance (hereinafter referred to as "user distance") between the display 35 and the user who is viewings the display 35. The distance specifying unit 25 includes a position specifying device for specifying the user distance. The position specifying device is, for instance, a camera, an infrared sensor, an optical sensor, etc. The distance specifying unit 25 sends the data of the specified user distance to the parallax calculator 26.

A series of processes up to the specifying of the inter-pupil distance and user distance by the inter-pupil distance specifying unit 24 and distance specifying unit 25 is referred to as "face recognition process". The face recognition process is executed in a mode selected by the user through the input unit 20. The execution modes of the face recognition process are, for example, a continuous mode, an intermittent mode, and a manual mode. These modes are properly changeable in accordance with a user instruction through the input unit 20. In addition, the execution modes of the inter-pupil distance specifying unit 24 and distance specifying unit 25 may be asynchronous. In the continuous mode, the inter-pupil distance specifying unit 24 always executes the face recognition process. In the intermittent mode, the inter-pupil distance specifying unit 24 executes the face recognition process at predetermined time intervals. The predetermined time interval is preset by the user, and can properly be varied in accordance with a user instruction through the input unit 20. In the manual mode, the inter-pupil distance specifying unit 24 executes the face recognition process at a timing desired by the user. For example, the timing is when a specific gesture movement is executed by the user, when a specific word is uttered by the user, when a specific sound is produced by the user, or when an operation through the input unit 20 is executed. The specific gesture movement, specific word and specific sound are a gesture, a word and a sound corresponding to commands (hereinafter referred to as "face recognition commands") of "Execution of face recognition process" registered in the command DB. Upon recognizing the specific gesture movement executed by the user, the gesture recognition section 23 sends the face recognition command to the inter-pupil distance specifying unit 24. Similarly, upon recognizing the specific word and specific sound produced by the user, the speech recognition section 22 sends the face recognition command to the inter-pupil distance specifying unit 24.

The parallax calculator 26 calculates the parallax (hereinafter referred to as "user parallax") which is inherent to the user, based on the inter-pupil distance of the user and the user distance. A reference position in the calculation of the user parallax is, for example, the center position of the display 35. For example, trigonometry is used for the calculation of the user parallax. Accordingly, in the case where the user moves in a manner to approach the display 35, the user parallax at a position after the movement becomes wider than the user parallax before the movement. The parallax calculator 26 sends the data relating to the calculated user parallax to the image selector 32 and imaging condition setting unit 27.

The imaging condition setting unit 27 sets the imaging condition of X-rays, based on the imaging condition of X-rays, which was input by the user through the input unit 20. In addition, the imaging condition setting unit 27 sets a plurality of imaging angles, based on the angle condition of X-ray imaging which was input by the user through the input unit 20, the line-of-sight angle and the parallax. The parallax used at this time may be either the fixed parallax or the user parallax. Either the fixed parallax or the user parallax, which is to be used, is selected in accordance with a user instruction through the input unit 20. The function relating to the setting of plural imaging angles by the imaging condition setting unit 27 is called "imaging angle setting function". The details of the imaging angle setting function will be described later.

The imaging controller 28 controls the high voltage generator 16 and moving unit 19, based on the X-ray imaging condition and imaging angle condition which were set by the imaging condition setting unit 27.

The preprocessor 29 executes a preprocess on an electric signal which was output from the X-ray detector 18. The preprocess is, for instance, a correction process of any kind, an amplification process, an A/D conversion process, etc.

The image generator 30 generates data of a plurality of X-ray images, based on the electric signal on which the preprocess was executed. Information relating to the imaging angle is added to the data of each X-ray image. A pixel value, which is allocated to each of pixels constituting the X-ray image, is, for example, a value corresponding to an X-ray attenuation coefficient relating to a substance on the transmission path of X-rays.

The memory unit 31 is a semiconductor memory or the like. The memory unit 31 temporarily stores data of two X-ray images selected from the storage unit 36 (to be described later) by the image selector 32. In addition, the memory unit 31 stores the data of the X-ray imaging condition, angle condition and line-of-sight angle. Incidentally, the memory unit 31 may store the X-ray imaging condition and angle condition as a condition DB, in accordance with a user instruction through the input unit 20. In the condition DB, the X-ray imaging condition is managed in a hierarchical manner, for example, by the age, body-build and gender of the subject, the imaging part, and the line-of-sight angle.

The memory unit 31 stores the command DB. The command DB is a DB for collating the shape of a gesture movement recognized by the gesture recognition unit 23 and the user speech recognized by the speech recognition unit 22.

Figure 4:
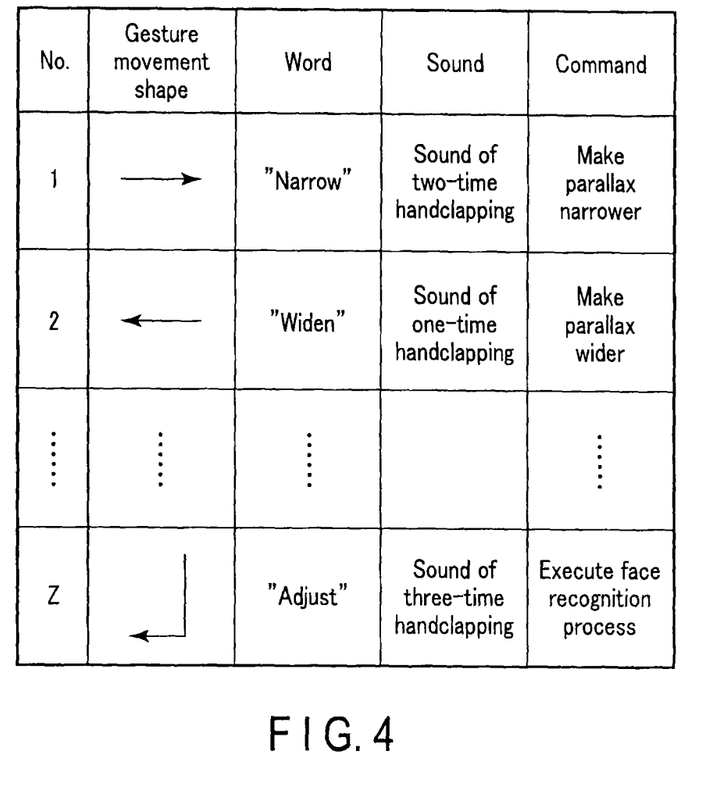
FIG. 4 is a view illustrating an example of a command DB which is stored in a memory unit of the X-ray diagnosis apparatus according to the embodiment.

FIG. 4 is a view illustrating an example of the command DB which is stored in the memory unit 31 of the X-ray diagnosis apparatus 1 according to the embodiment. As illustrated in FIG. 4, the command DB is a DB in which a plurality of gesture movement shapes, a plurality of words and a plurality of sounds are associated with a plurality of commands. The commands are, for instance, "Make parallax narrower", "Make parallax wider", and "Execute face recognition process".

The storage unit 36 is a semiconductor memory device, such as a Flash SSD (Solid State Disk) that is a semiconductor memory element, and an HDD (Hard Disk Drive). The storage unit 36 stores data of a plurality of X-ray images with different imaging angles. The data of the plural X-ray images are classified into a left-eye image group and a right-eye image group. The left-eye image group is an image group including a plurality of X-ray images captured at a plurality of imaging angles included in a left-eye angle region (to be described later). In addition, the right-eye image group is an image group including a plurality of X-ray images captured at a plurality of imaging angles included in a right-eye angle region (to be described later). Two X-ray images included in the respective angle regions, which have substantially the same angular difference from the line-of-sight angle, are mutually associated. In the case where the medical image display apparatus 2 is an independent apparatus, the storage unit 36 may be an external device which is connected to the medical image display apparatus 2 via a public network such as the Internet.

In accordance with the user parallax or fixed parallax, the image selector 32 selects a left-eye image and a right-eye image, respectively, from the left-eye image group and right-eye image group stored in the storage unit 36. The data of the left-eye image and the data of the right-eye image, which were selected by the image selector 32, are temporarily stored in the memory unit 31. In addition, the image selector 32 receives a command instructing switching of a displayed image (hereinafter referred to as "image switching command), the command being sent from the speech recognition unit 22 and gesture recognition unit 23. In accordance with this command, the image selector 32 selects the corresponding left-eye image and right-eye image from the left-eye image group and right-eye image group stored in the storage unit 36. The details relating to the image selection process by the image selector 32 will be described later.

The controller 33 includes a CPU (Central Processing Unit) and a memory circuit. The controller 33 receives instruction information which was input through the input unit 20, and temporarily stores the instruction information in the memory circuit. Based on the input information, the controller 33 controls the respective components of the X-ray diagnosis apparatus 1. Specifically, the controller 33 classifies the data of plural X-ray images generated by the image generator 30 into the left-eye image group and right-eye image group in accordance with the data relating to the imaging angle that is added to each of the X-ray images, and stores the left-eye image group and right-eye image group in the storage unit 36.

The display controller 34 reads out, from the memory unit 31, the data of the left-eye image and the data of the right-eye image, which were selected by the image selector 32 and are temporarily stored in the memory unit 31, and displays stereoscopic video relating to the line of sight on the display 35 (to be described later).

For example, in a naked-eye-type 2-parallax lenticular lens method, the display controller 34 sends to the display 35 a video signal in which the left-eye image and right-eye image are vertically divided in strip shapes. The display 35 displays the left-eye image and right-eye image which are vertically divided in strip shapes, such that the divided left-eye image and right-eye image are alternately arranged. The divided left-eye image and right-eye image are alternately arranged and displayed on the display 35. The display 35 includes a lenticular lens on the display surface. The lenticular lens is a lens which varies a position which the line of sight reaches, depending on the position of view of the user. By adjusting the disposition of the lenticular lens, the right eye views only the right-eye image, and the left eye views only the left-eye image, and thus stereopsis is realized.

In addition, in a glasses-type frame sequential method, the display controller 34 transmits to the display 35 a right-eye image signal following a left-eye image signal within a 1-frame synchronization period. Based on the transmitted image signals, the display 35 displays an image. The user wears liquid-crystal shutter glasses, and views the display 35. The liquid-crystal shutter alternately shuts the left and right view fields in synchronism with the display operation by the display 35. Since the shutter of the glasses opens and closes in complete synchronism with the two images, the right eye views only the right-eye image and the left eye views only the left-eye image, and therefore stereopsis is realized.

The two stereopsis methods have been described by way of example in connection with the display controller 34 and display 35 of the embodiment. However, the present embodiment is applicable to any stereopsis method which utilizes parallax. In addition, the embodiment is also applicable to a stereopsis method which can utilize multiple parallaxes.

Figure 5:
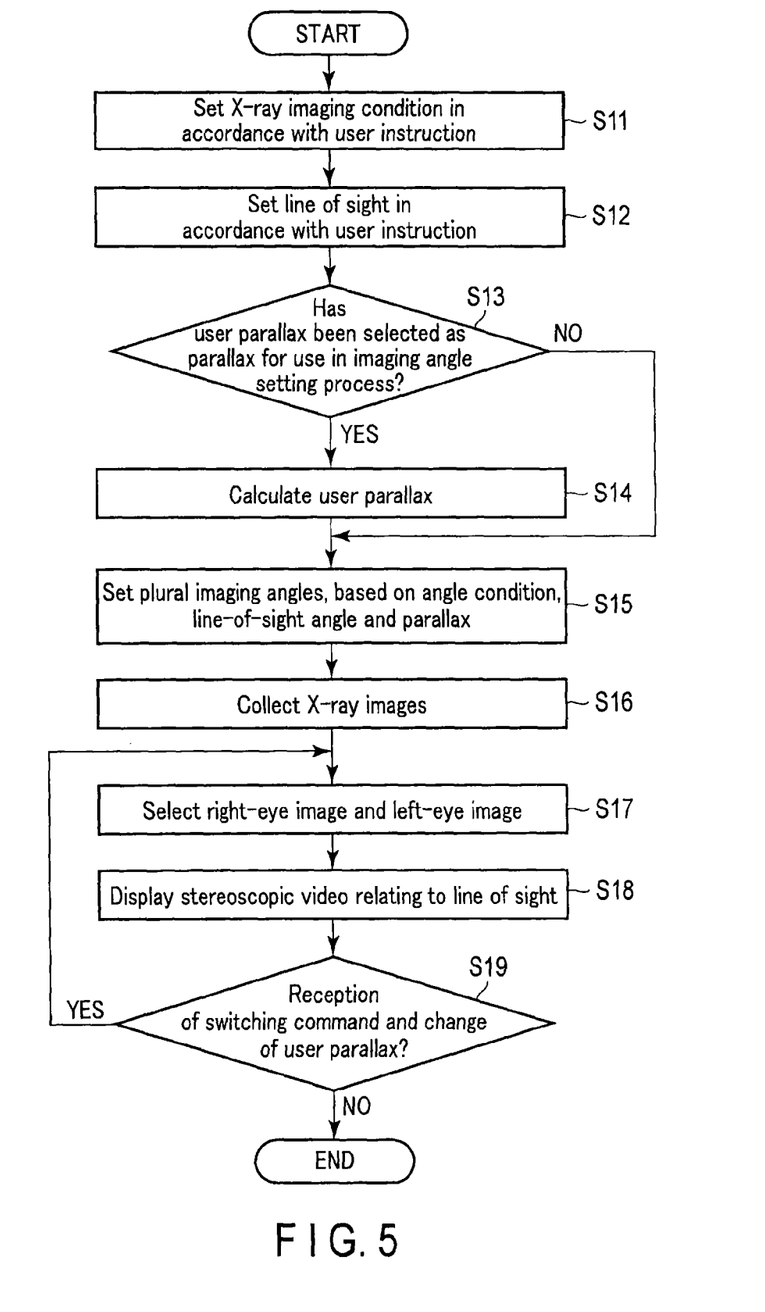
FIG. 5 is a flowchart illustrating an example of a flow of a series of processes using the X-ray diagnosis apparatus according to the embodiment.

Next, referring to FIG. 5, a description is given of a process using the X-ray diagnosis apparatus 1 according to the present embodiment.

FIG. 5 is a flowchart illustrating an example of a flow of a series of processes using the X-ray diagnosis apparatus 1 according to the embodiment.

(Step S11)

In accordance with a user instruction through the input unit 20, the imaging condition of X-rays is set by the imaging condition setting unit 27.

(Step S12)

The line of sight, which was input by the user through the input unit 20, is accepted. Specifically, by operating the operation board of the input unit 20, the user moves the C-shaped arm 11 such that the imaging axis agrees with the line of sight. Then, with the user having pressed the button which relates to the determination of the line of sight and is provided on the operation board, the line of sight is determined. In addition, the line of sight may be determined in accordance with a user instruction on the image for alignment, which relates to the subject displayed on the display 35. If the line of sight is determined, the angle detector 21 detects the line-of-sight angle corresponding to the line of sight. The data relating to the detected line-of-sight angle is sent to the imaging condition setting unit 27.

(Step S13)

The parallax for setting the imaging angle is selected by the user from the user parallax and the fixed parallax. When the user parallax has been selected, the process advances to step S14. When the fixed parallax has been selected, the process goes to step S15.

(Step S14)

The user parallax is calculated by the inter-pupil distance specifying unit 24, distance specifying unit 25 and parallax calculator 26.

(Step S15)

Based on the angle condition which was input by the user through the input unit 20, the line-of-sight angle and the parallax, a plurality of imaging angles are automatically set by the imaging angle setting function of the imaging condition setting unit 27 (to be described later).

(Step S16)

In accordance with a user instruction through the input unit 20, X-ray imaging is started by the respective components. Then, under the X-ray imaging condition set by the imaging condition setting unit 27, X-ray images captured at the set imaging angle are collected by the respective components. The data of the collected plural X-ray images are stored in the storage unit 36 together with the information relating to the imaging angle, which is added to each X-ray image.

(Step S17)

By the image selector 32, the left-eye image and right-eye image are selected from the left-eye image group and the right-eye image group.

(Step S18)

Based on the left-eye image and right-eye image selected by the image selector 32, the display controller 34 causes the display 35 to display stereoscopic video relating to the line of sight. The user performs diagnosis, medical treatment, etc., while viewing the stereoscopic video displayed on the display 35.

(Step S19)

Upon receiving a switching command, the process shifts to the selection of the image by the image selector 32 in step S17. In addition, when the data relating to the user parallax was received and it was detected that the user parallax was changed, the process shifts to the selection of the image by the image selector 32 in step S17. Each time the reception of the switching command and the change of the user parallax occur, the process of step S17 and step S18 is repeatedly executed. The function corresponding to the process of steps S17 to S19 included in the X-ray diagnosis apparatus 1 is called "auto-adjustment function" (to be described later). The details of the auto-adjustment function will be described later.

(Imaging Angle Setting Function)

The imaging angle setting function is a function in which the imaging condition setting unit 27 of the X-ray diagnosis apparatus 1 according to the embodiment automatically sets a plurality of imaging angles, based on the angle condition which was input by the user through the input unit 20, the line-of-sight angle and the parallax. A process according to the imaging angle setting function (hereinafter referred to as "imaging angle setting process") is described with reference to FIG. 6.

Figure 6:
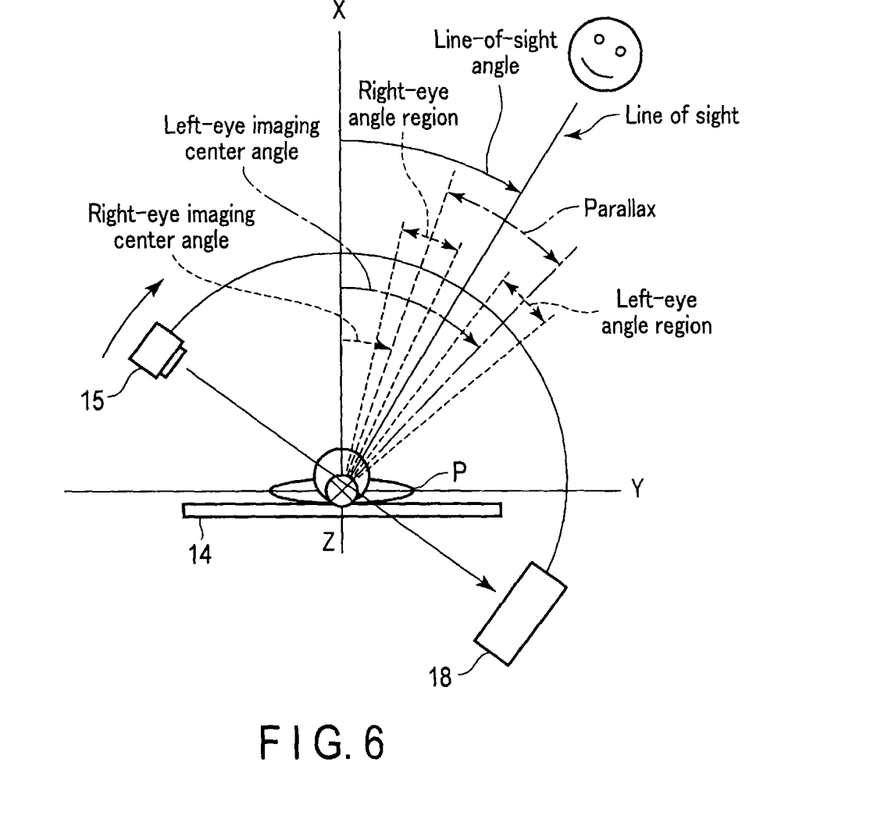
FIG. 6 is an explanatory view for explaining an imaging angle setting process by an imaging condition setting unit of the X-ray diagnosis apparatus according to the embodiment.

FIG. 6 is an explanatory view for explaining the imaging angle setting process by the imaging condition setup unit 27 of the X-ray diagnosis apparatus 1 according to the embodiment. Incidentally, in the description of the imaging angle setting process, it is assumed that the fixed parallax was selected in step S13 in FIG. 3. In addition, for the purpose of simple description, it is assumed that the first angle θ, which forms the line-of-sight angle, is 0°. In the meantime, the imaging angle setting process is also applicable to cases in which the first angle θ is not 0°.

To begin with, the imaging condition setup unit 27 sets, based on the fixed parallax and line-of-sight angle, an imaging center angle in a left-eye angle region (hereinafter referred to as "left-eye imaging center angle") and an imaging center angle in a right-eye angle region (hereinafter referred to as "right-eye imaging center angle"). For example, in the case in which the line-of-sight angle (first angle θ) is 45° and the fixed parallax is 4°, the imaging condition setup unit 27 sets the left-eye imaging center angle at 47° and sets the right-eye imaging center angle at 43°. An imaging position corresponding to the line-of-sight angle, an imaging position corresponding to the left-eye imaging center angle and an imaging position corresponding to the right-eye imaging center angle are provided at positions along the imaging rotational direction.

Then, if the imaging center angles are set as described above, a plurality of imaging angles are set in each angle region in accordance with the angle condition. For example, in the case in which the interval of imaging angles is 0.1° and the number of times of imaging in each angle region is 11, the imaging condition setting unit 27 sets a plurality of imaging angles in the left-eye angle region over a range of $\varphi=42.5°~43.5°$ at intervals of 0.1°. In addition, the imaging condition setting unit 27 sets a plurality of imaging angles in the right-eye angle region over a range of $\varphi=46.5°~47.5°$ at intervals of 0.1°. Then, an imaging angle in the left-eye angle region and an imaging angle in the right-eye angle region, which have the same angular difference from the line-of-sight angle, are associated. For example, the imaging angle $\varphi=42.6°$ in the left-eye angle region and the imaging angle $\varphi=47.4°$ in the right-eye angle region are mutually associated since these imaging angles have the same angular difference of 2.4° from the line-of-sight angle 45°.

By the above-described imaging angle setting process of the imaging condition setting unit 27, the left-eye angle region and right-eye angle region, the center between which is set at the line-of-sight angle, are set. In addition, the angular difference of each of the imaging angles included in the left-eye angle region, from the line-of-sight angle, substantially agrees with the angular difference of each of the imaging angles included in the right-eye angle region, from the line-of-sight angle.

(Auto-Adjustment Function)

The auto-adjustment function is a function in which the image selector 32 of the X-ray diagnosis apparatus 1 according to the embodiment automatically selects a left-eye image and a right-eye image from the left-eye image group and right-eye image group, respectively, upon the reception of the switching command and the detection of the change of the user parallax. Referring to FIG. 7 and FIG. 8, a process according to the auto-adjustment function (hereinafter referred to as "auto-adjustment process") is described. Incidentally, ON/OFF of the auto-adjustment function can be switched, when necessary, in accordance with a user instruction through the input unit 20. In addition, ON/OFF can also be switched, when necessary, by a user's gesture, voice, the occurrence of sound, etc.

FIG. 7 is explanatory views for explaining a timing at which the auto-adjustment process of the X-ray diagnosis apparatus 1 according to the embodiment is executed. As illustrated in FIG. 7, the auto-adjustment process is executed, for example, at a time of a user distance change (FIG. 7A), at a time of a user change (FIG. 7B), at a time of execution of a specific gesture movement by the user (FIG. 7C), and at a time of utterance of a specific word by the user (FIG. 7D). Specifically, in the case where the user distance was changed, as illustrated in FIG. 7A, the user distance is first specified by the distance specifying unit 25. Then, the inter-pupil distance is specified by the inter-pupil distance specifying unit 24. Based on the user distance and the inter-pupil distance, the user parallax is calculated by the parallax calculator 26. The information relating to the calculated user parallax is sent to the image selector 32. Incidentally, in the auto-adjustment process, the execution mode of the distance specifying unit 25 and inter-pupil distance specifying unit 24 may be any one of the above-described modes. Also in the case where the user was changed, as illustrated in FIG. 7B, the same process as the process of FIG. 7A is executed by the respective components.

Figure 7A:
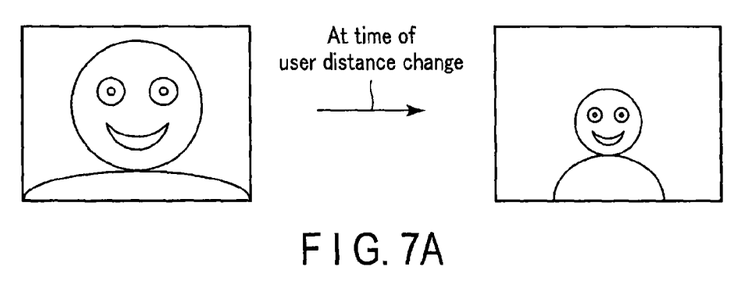
FIG. 7A is a first explanatory view for explaining a timing at which an auto-adjustment process of the X-ray diagnosis apparatus according to the embodiment is executed.
Figure 7B:
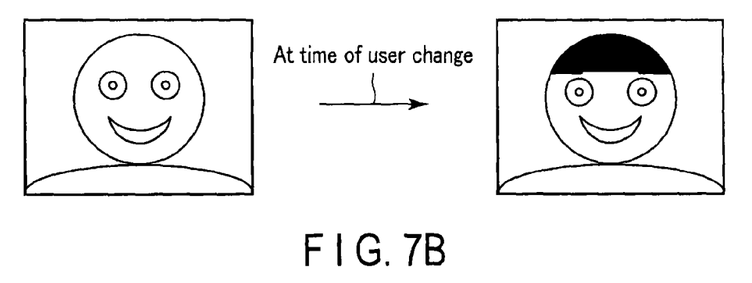
FIG. 7B is a second explanatory view for explaining a timing at which the auto-adjustment process of the X-ray diagnosis apparatus according to the embodiment is executed.
Figure 7C:
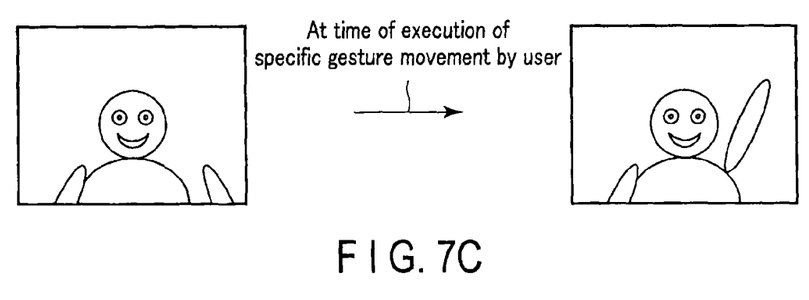
FIG. 7C is a third explanatory view for explaining a timing at which the auto-adjustment process of the X-ray diagnosis apparatus according to the embodiment is executed.
Figure 8:
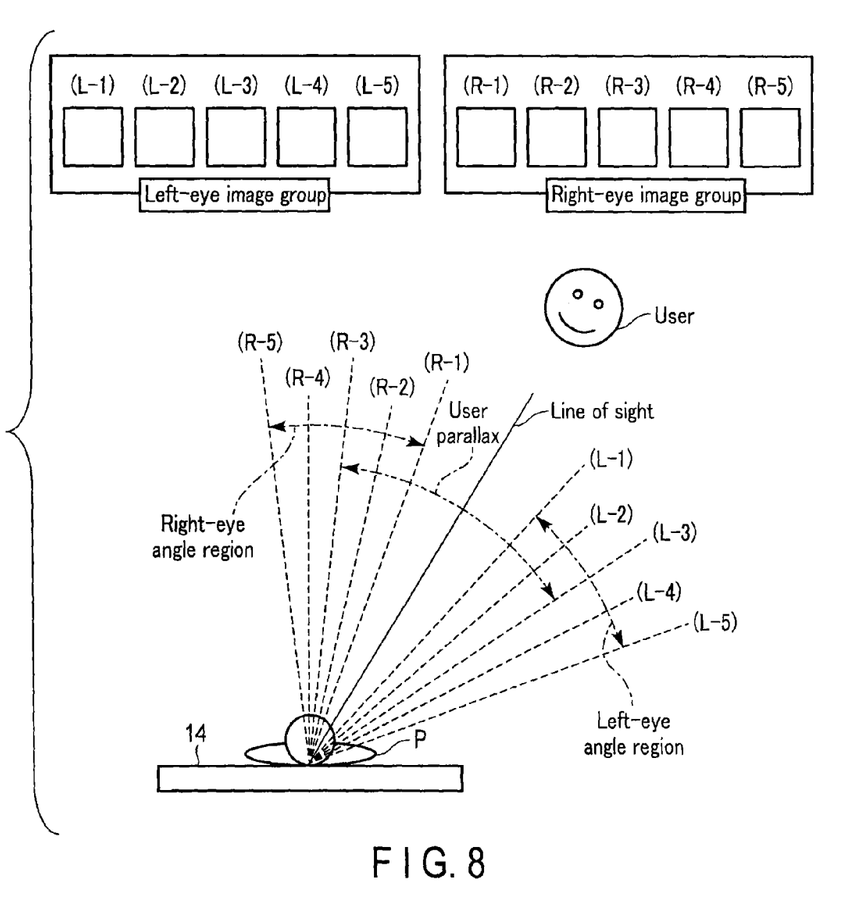
FIG. 8 is an explanatory view for explaining a selection process by an image selector of the X-ray diagnosis apparatus according to the embodiment.

In addition, in the case where a specific gesture movement was executed by the user, as illustrated in FIG. 7C, this specific gesture movement is recognized by the gesture recognition unit 23, and a signal relating to the corresponding switching command is sent to the image selector 32.

Figure 7D:
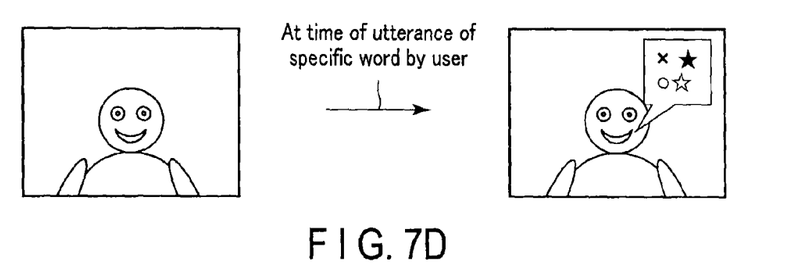
FIG. 7D is a fourth explanatory view for explaining a timing at which the auto-adjustment process of the X-ray diagnosis apparatus according to the embodiment is executed.

Furthermore, in the case where the user's specific sound was produced, as illustrated in FIG. 7D, the user's specific sound is detected by the speech recognition unit 22, and a signal relating to the corresponding switching command is sent to the image selector 32. The specific sound is, for instance, a specific word uttered by the user, and a specific sound produced by the user.

Next, referring to FIG. 8, the image selection process by the image selector 32 is described.

FIG. 8 is an explanatory view for explaining the selection process by the image selector 32 of the X-ray diagnosis apparatus 1 according to the embodiment. In the description of FIG. 8, it is assumed that ten images are stored in the storage unit 36. The ten images are classified into a left-eye image group and a right-eye image group. Five images with consecutive imaging angles are included in each of the left-eye image group and right-eye image group. Of the five images of the left-eye image group and the five images of the right-eye image group, two images having the same angular difference from the line-of-sight angle are mutually associated. For example, an image (L-1) of the left-eye image group and an image (R-1) of the right-eye image group have the same angular difference from the line-of-sight angle, and are mutually associated. Accordingly, in the description of FIG. 8, the storage unit 36 stores five image sets each consisting of two images having the angular difference from the line-of-sight angle. Of the five image sets, an image set 1, which is composed of the image (L-1) and image (R-1), has a least angular difference (parallax), and an image set 5, which is composed of an image (L-5) and an image (R-5), has a greatest angular difference (parallax). The angular differences gradually increase in the order of the image set 1 to image set 5. Incidentally, it is assumed that the image set 3 (image (L-3) and image (R-3)) is displayed as the initial state on the display 35 by the display controller 34 for stereopsis by the user.

Upon receiving the switching command that was sent from the gesture recognition unit 23 and speech recognition unit 22, the image selector 32 selects an image set (one image from the left-eye image group and one image from the right-eye image group) corresponding to the switching command, from the plural image sets (plural images) stored in the storage unit 36. For example, upon receiving a switching command relating to "Make parallax narrower", the image selector 32 selects, from the storage unit 36, an image set having an angular difference (parallax) which is narrower than an angular difference (parallax) of the image set that is currently displayed on the display 35. Specifically, the image selector 32 selects the image set 2 having an angular difference (parallax) which is next narrower than the angular difference (parallax) of the image set 3 that is currently displayed on the display 35. The image controller 34 displays the image set 3, which was selected by the image selector 32, on the display 35 for stereopsis by the user.

In addition, the image selector 32 receives the data relating to the user parallax that was sent from the parallax calculator 26, and selects an image set (a left-eye image and a right-eye image) corresponding to this parallax (one image from the left-eye image group and one image from the right-eye image group), from the plural image sets stored in the storage unit 36. Specifically, the image selector 32 detects whether a change occurred to the received user parallax from the user parallax before the reception. Then, if the received user parallax is different from the user parallax before the reception, the image selector 32 selects an image set (a left-eye image and a right-eye image) having an angular difference closest to the user parallax, from the plural image sets (left-eye image group and right-eye image group) stored in the storage unit 36.

According to the above-described imaging angle setting function, the following advantageous effects can be obtained.

The X-ray diagnosis apparatus 1 according to the embodiment, which includes the imaging angle setting function, can set a plurality of imaging angles, based on the angle condition, the fixed parallax (or user parallax) and the line-of-sight angle. The plural imaging angles are classified into the left-eye angle region and right-eye angle region, the center between which is set at the line-of-sight angle. In addition, the plural angular differences corresponding to the plural imaging angles included in the left-eye angle region substantially agree with the plural angular differences corresponding to the plural imaging angles included in the right-eye angle region. The X-ray diagnosis apparatus 1 according to the embodiment, which stores a plurality of X-ray images captured at the plural imaging angles set by the imaging angle setting function, can execute such display as to enable the user to stereoscopically recognize the subject, without executing imaging once again even when the user was changed or the user moved. Therefore, the X-ray diagnosis apparatus 1 according to the embodiment, which includes the imaging angle setting function, can realize an improvement in work efficiency in diagnosis, medical treatment, etc., using a technique of image stereopsis.

In addition, according to the above-described auto-adjustment function, the following advantageous effects can be obtained.

The X-ray diagnosis apparatus 1 according to the embodiment, which includes the auto-adjustment function, can automatically specify the angular difference (parallax) at which the user can stereoscopically recognize the subject, in accordance with the distance of the user to the display 35 or the change of the user. Furthermore, in accordance with the variation in user distance and the change of the user, the image set (left-eye image and right-eye image) having an optimal angular difference can automatically be displayed on the display 35. Accordingly, even when the user was changed or the user moved, the user can stereoscopically recognize the subject by viewing the display 35. In addition, at a timing when a specific gesture movement has been executed by the user, at a timing when a specific word has been uttered by the user, and at a timing when a specific sound has been produced by the user, the image set (left-eye image and right-eye image), which is being displayed, can automatically be changed. Therefore, the user can recognize a stereoscopic image of the subject, which agrees with the individual sensitivity of the user. By the above-described advantageous effects, the X-ray diagnosis apparatus 1 according to the embodiment, which includes the auto-adjustment function, can realize an improvement in work efficiency in diagnosis, medical treatment, etc.

While certain embodiments have been described, these embodiments have been presented by way of example only, and are not intended to limit the scope of the inventions. Indeed, the embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image display apparatus which is accessible to an external device that stores data of a plurality of X-ray images with different imaging angles, or includes a storage unit that stores the data of the plurality of X-ray images, comprising:
a display; and
a controller configured to
specify a distance of a user to the display;
specify an inter-pupil distance of the user;
select, from the plurality of X-ray images, two X-ray images with an angular difference determined based on the distance of the user and the inter-pupil distance of the user; and
display the selected two X-ray images on the display for stereopsis by the user.

2. The medical image display apparatus of claim 1, wherein the plurality of X-ray images are classified into a left-eye image group and a right-eye image group.

3. The medical image display apparatus of claim 2, wherein the controller is configured to select one of the two X-ray images from the left-eye image group and select another of the two X-ray images from the right-eye image group.

4. The medical image display apparatus of claim 1, wherein the controller is further configured to
recognize a gesture of the user; and
reselect, from the plurality of X-ray images, two X-ray images in accordance with the gesture of the user.

5. The medical image display apparatus of claim 1, wherein the controller is further configured to
recognize at least one of a word uttered by the user and a sound produced by the user; and
reselect, from the plurality of X-ray images, two X-ray images in accordance with at least one of the word uttered by the user and the sound produced by the user.

6. An X-ray diagnosis apparatus comprising:
an X-ray generator that generates X-rays;
an X-ray detector that detects the X-rays which were generated from the X-ray generator and passed through a subject;
a mover that moves the X-ray generator and the X-ray detector to a plurality of imaging angles such that the X-ray generator and the X-ray detector are opposed to each other;
a display; and
a controller configured to
accept an input of a direction of stereopsis of the subject;
specify a distance of a user to the display;
specify an inter-pupil distance of the user; and
set the plurality of imaging angles, based on the direction of the stereopsis, the distance of the user and the inter-pupil distance.

7. A method of stereoscopically displaying a medical image, the method comprising:
obtaining data of a plurality of X-ray images with different imaging angles,
specifying a distance of a user to a display;
specifying an inter-pupil distance of the user;
selecting, from the plurality of X-ray images, two X-ray images with an angular difference determined based on the distance of the user and the inter-pupil distance of the user; and
controlling the display to display the selected two X-ray images for stereopsis by the user.

8. The method according to claim 7, further comprising:
classifying the plurality of X-ray images into a left-eye image group and a right-eye image group.

9. The method according to claim 8, further comprising:
selecting one of the two X-ray images from the left-eye image group, and
selecting another of the two X-ray images from the right-eye image group.

10. The method according to claim 7, further comprising:
recognizing a gesture of the user; and
reselecting, from the plurality of X-ray images, two X-ray images in accordance with the gesture of the user.

11. The method according to claim 7, further comprising:
recognizing at least one of a word uttered by the user and a sound produced user, and
reselecting, from the plurality of X-ray images, two X-ray images in accordance with at least one of the word uttered by the user and the sound produced by the user.

12. A method of stereoscopically displaying a medical image, the method comprising:
generating, using an X-ray generator, X-rays
detecting, using an X-ray detector, the generated X-rays after the generated X-rays have passed through a subject;
accepting an input of a direction of stereopsis of the subject;
specifying a distance of a user to the display;
specifying an inter-pupil distance of the user;
setting a plurality of imaging angles, based on the direction of the stereopsis, the distance of the user, and the inter-pupil distance; and
moving the X-ray generator and the X-ray detector to the plurality of imaging angles, the X-ray generator and the X-ray detector being opposed to each other.

* * * * *